（12） United States Patent
Hashino et al.

(10) Patent No.: US 9,023,007 B2
(45) Date of Patent: May 5, 2015

(54) WEARING ARTICLE WITH DIFFERENTIAL TIGHTENING FORCES IN THE WAIST REGIONS

(75) Inventors: Yuki Hashino, Kagawa (JP); Sarinee Phichetkitjawat, Kagawa (JP); Shunsuke Masaki, Kagawa (JP)

(73) Assignee: Unicharm Corporation, Ehime (JP)

( * ) Notice: Subject to any disclaimer, the term of this patent is extended or adjusted under 35 U.S.C. 154(b) by 350 days.

(21) Appl. No.: 13/519,622

(22) PCT Filed: Dec. 16, 2010

(86) PCT No.: PCT/JP2010/072644
§ 371 (c)(1),
(2), (4) Date: Jun. 28, 2012

(87) PCT Pub. No.: WO2011/081027
PCT Pub. Date: Jul. 7, 2011

(65) Prior Publication Data
US 2012/0289921 A1    Nov. 15, 2012

(30) Foreign Application Priority Data

Dec. 28, 2009  (JP) .................................. 2009-298787

(51) Int. Cl.
*A61F 13/49*   (2006.01)
*A61F 13/496*  (2006.01)
*A61F 13/494*  (2006.01)

(52) U.S. Cl.
CPC .......... *A61F 13/496* (2013.01); *A61F 13/49406* (2013.01); *A61F 13/49413* (2013.01); *A61F 13/49011* (2013.01); *A61F 13/49019* (2013.01)

(58) Field of Classification Search
CPC ................... A61F 13/49007; A61F 13/49009; A61F 13/49011; A61F 13/49014; A61F 13/49019; A61F 2013/49028; A61F 2013/49033; A61F 2013/49038

USPC ..................... 604/385.24, 385.29, 385.3, 394
See application file for complete search history.

(56) References Cited

U.S. PATENT DOCUMENTS

2011/0106039 A1* 5/2011 Saito et al. ................. 604/385.3
2011/0178489 A1* 7/2011 Baba et al. ................. 604/385.3

FOREIGN PATENT DOCUMENTS

| JP | 10-314220 A | 12/1998 |
| JP | 2009-165839 A | 7/2009 |
| JP | 2009-240694 A | 10/2009 |
| JP | 2009-240695 A | 10/2009 |
| WO | WO 2008153144 A1 * | 12/2008 |
| WO | WO 2009/122803 A1 | 10/2009 |
| WO | WO 2009122803 A1 * | 10/2009 |

OTHER PUBLICATIONS

International Search Report from corresponding PCT application No. PCT/JP2010/072644 dated Mar. 29, 2011 (3 pgs).

* cited by examiner

*Primary Examiner* — Jackie T Ho
*Assistant Examiner* — Kathryn E Ditmer
(74) *Attorney, Agent, or Firm* — Brinks Gilson & Lione

(57) ABSTRACT

A wearing article configured to smooth out wrinkles that tend to be created in front and rear waist regions. A diaper includes front and rear waist members connected to an intermediary crotch. The front and rear waist members extend from waist ends toward the side of a crotch region and respectively include first regions overlapping front and rear end flaps of the absorbent structure and second regions adjacent the respective first regions. In the front and rear waist members, the first regions and the second regions are provided with first and second waist elastic members sandwiched between the respective top- and backsheets. The respective second regions are formed with inelastic zones overlapping the core and elastic regions lying on both sides of the inelastic regions in the transverse direction. The tightening force of the first regions are lower than the tightening force of the respective second regions.

3 Claims, 6 Drawing Sheets

WEARING ARTICLE WITH DIFFERENTIAL TIGHTENING FORCES IN THE WAIST REGIONS

RELATED APPLICATION

This application is a 35 U.S.C. §371 national phase filing of International Patent Application No. PCT/JP2010/072644, filed Dec. 16, 2010, through which and to which priority is claimed under 35 U.S.C. §119 to Japanese Patent Application No. 2009-298787, filed Dec. 28, 2009.

TECHNICAL FIELD

The present invention relates to wearing articles and more particularly to wearing articles such as disposable diapers, toilet-training pants incontinent briefs and the like.

BACKGROUND

Conventionally, disposable diapers being formed with a waist-opening and leg-openings and in which the waist-opening is provided along a periphery thereof with waist elastic members are known. For example, the diaper disclosed in JP 10-314220A (PTL 1) includes an upper waist gathered region formed in the vicinity of the waist-opening, a lower waist gathered region formed adjacent the upper waist surrounding gathered region on the side of the crotch region and a liquid-absorbent structure partially overlapping the lower waist gathered region.

CITATION LIST

Patent Literature

{PTL 1} JP 10-314220 A

SUMMARY

Technical Problem

The upper waist gathered region and the lower waist gathered region are formed of the top- and backsheets and the elastic members sandwiched between these sheets. Under the effect of these elastic members, the top- and backsheets necessarily form a plurality of wrinkles extending in a longitudinal direction of the diaper. While these wrinkles should be smoothed merely by putting the diaper on the wearer's body, a longitudinal dimension from the waist-opening to the liquid-absorbent structure is relatively large and therefore it has been difficult for such a diaper to smooth these wrinkles over the entire length thereof.

An object of the present invention is to provide a wearing article improved to facilitate the wrinkles created in the front waist region as well as in the rear waist region to be smoothed.

Solution to Problem

According to the present invention, there is provided a wearing article having a longitudinal direction and a transverse direction and including:

a chassis including a side facing the wearer's body, a side facing the wearer's garment, a front waist region, a rear waist region and a crotch region extending between the front and rear waist regions;

a liquid-absorbent structure extending across the crotch region into the front and rear waist region; and waist elastic members attached to the front and rear waist regions under tension and in a contractible manner in the transverse direction wherein the liquid-absorbent structure includes a liquid-absorbent core, a cover sheet used to cover the core and front and rear end flaps lying outside front and rear ends of the core as viewed in the longitudinal direction and formed of the cover sheet.

The features according to the present invention reside in that:

the liquid-absorbent structure overlapping the front and rear waist regions has a dimension in the transverse direction corresponding to 70 to 90% of a dimension in the longitudinal direction of respective the front and rear waist regions and the front and rear waist regions extend from a waist-opening end to the side of the crotch region and at least include first regions at least partially overlapping the front and rear end flaps and second regions extending adjacent the first regions; and the first regions are elasticized over the entire area thereof by first waist elastic members in the transverse direction, the second regions respectively include inelastic zones overlapping the core and elastic zones lying outside the inelastic zones outside as viewed in the transverse direction and elasticized by second waist elastic members wherein tightening force of the first regions are set to be lower than that of the second regions.

According to one embodiment of the present invention, the tightening force of the first regions corresponds to 70 to 90% of the tightening force of the second regions.

According to another embodiment of the present invention, the front and rear waist regions are respectively divided into the first regions and the second regions.

According to still another embodiment of the present invention, the front and rear waist regions respectively include third regions extending adjacent the second regions on the side of the crotch region, the front and rear waist regions respectively divided into the first regions, the second regions and the third regions and the tightening force of the third regions is set to be lower than that of the second regions.

According to yet another embodiment of the present invention, the tightening force of the second regions is set to be higher than that of the third regions by 20 to 50%.

Advantageous Effects of Invention

According to the present invention, the liquid-absorbent structure overlapping the front and rear waist regions has a dimension in the transverse direction corresponding to 70 to 90% of a dimension in the longitudinal direction of respective the front and rear waist regions and the front and rear waist regions are respectively divided into the first regions lying in the vicinity of the waist-opening and second regions extending from the first regions toward the crotch region wherein the respective first regions have the tightening force set to be lower than that of the respective second regions. With such design, the wrinkles of the first regions can be easily smoothed as the waist-opening is broadened. The absorbent core overlaps the second regions and the inelastic zones are formed in such overlapping zones so as to restrict creation of the wrinkles in the second regions.

DESCRIPTION OF EMBODIMENTS

First Embodiment

FIGS. 1 through 5 illustrate the first embodiment of the present invention and details thereof will be more fully understood from the description of a disposable diaper as one example of the invention given hereunder with reference to these FIGS. 1 through 5.

Figure 1:
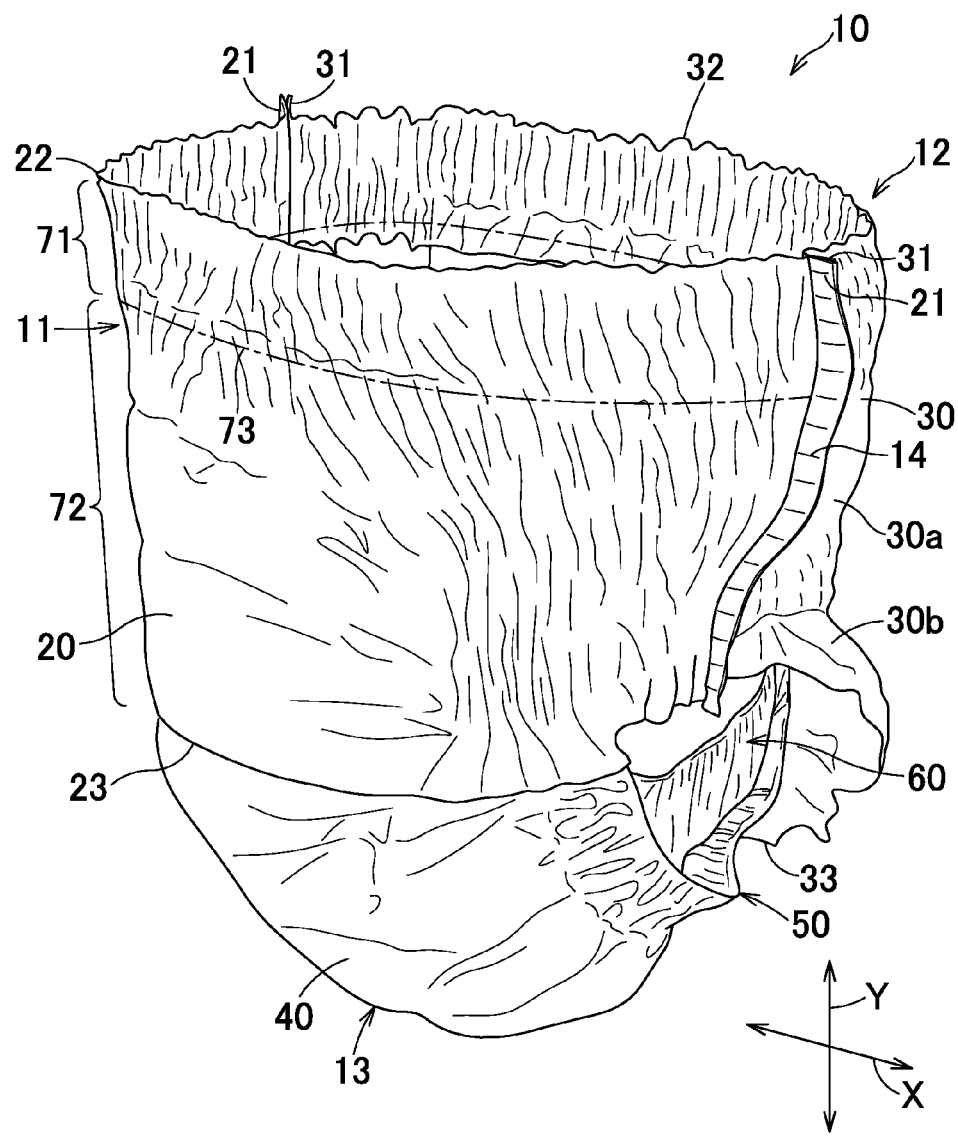
FIG. 1 is a perspective view of a diaper as one example of wearing articles.
Figure 2:
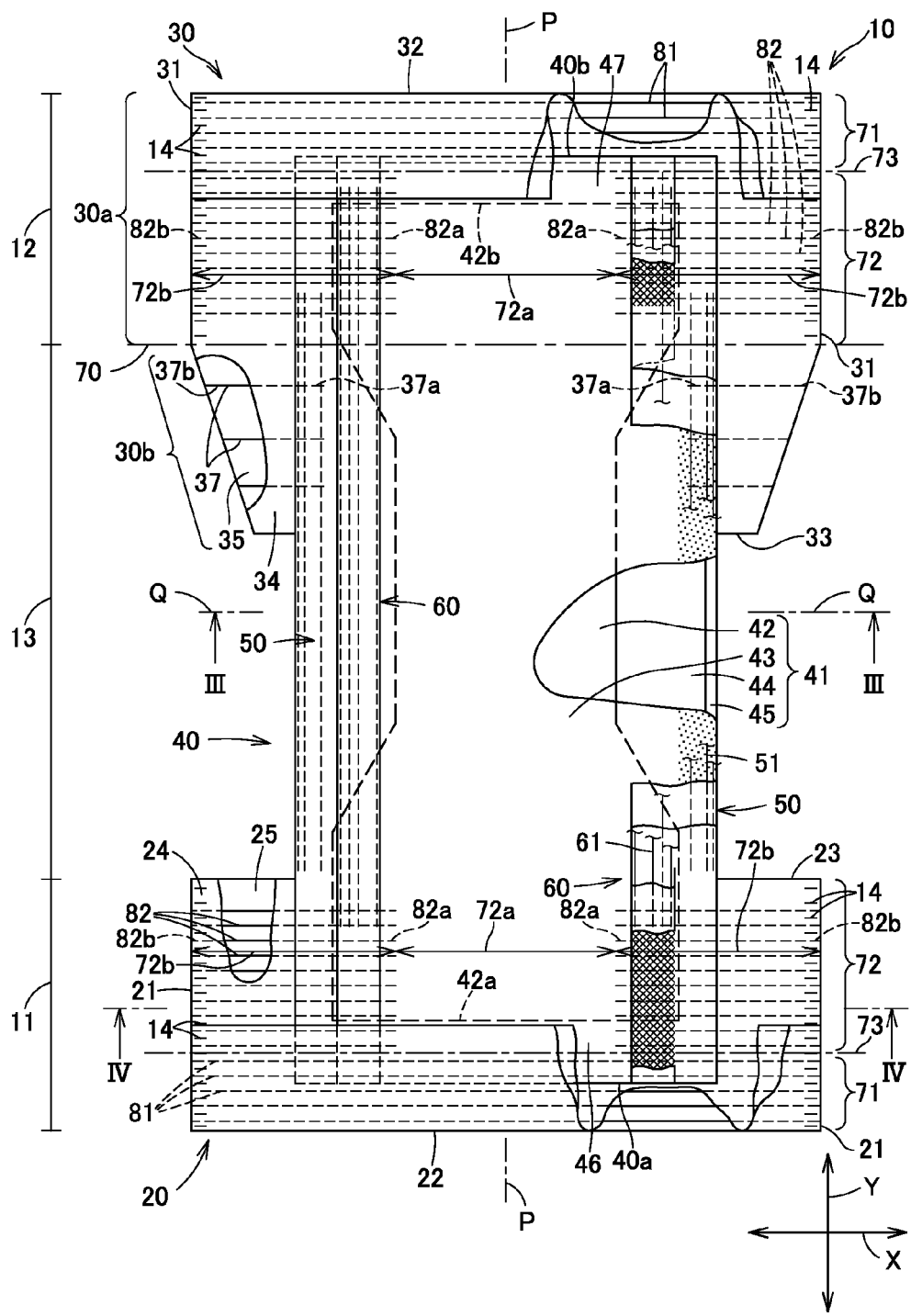
FIG. 2 is a developed plan view of the diaper according a first embodiment of the present invention as viewed from a side facing the wearer's body.
Figure 3:
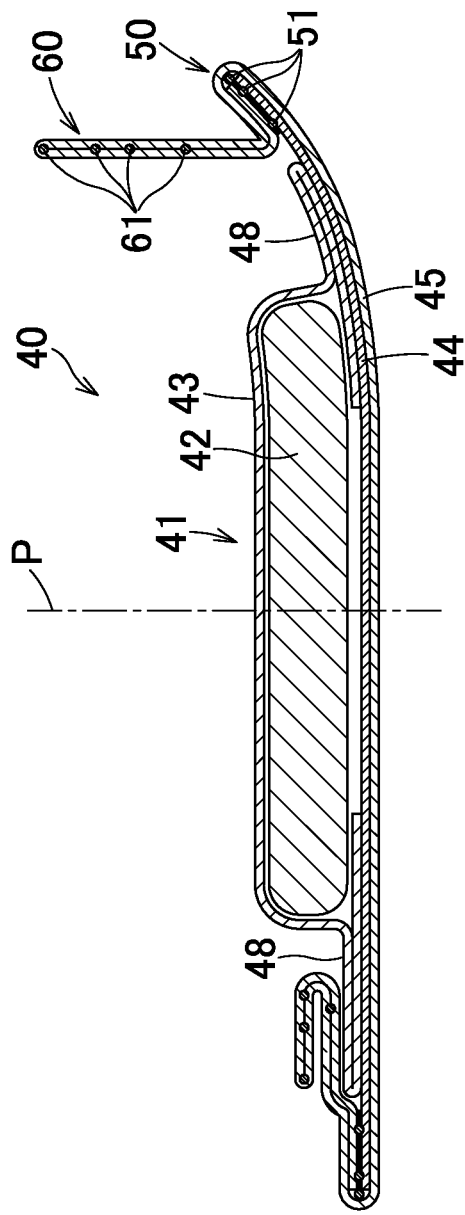
FIG. 3 is a sectional view taken along the line in FIG. 2.
Figure 4:
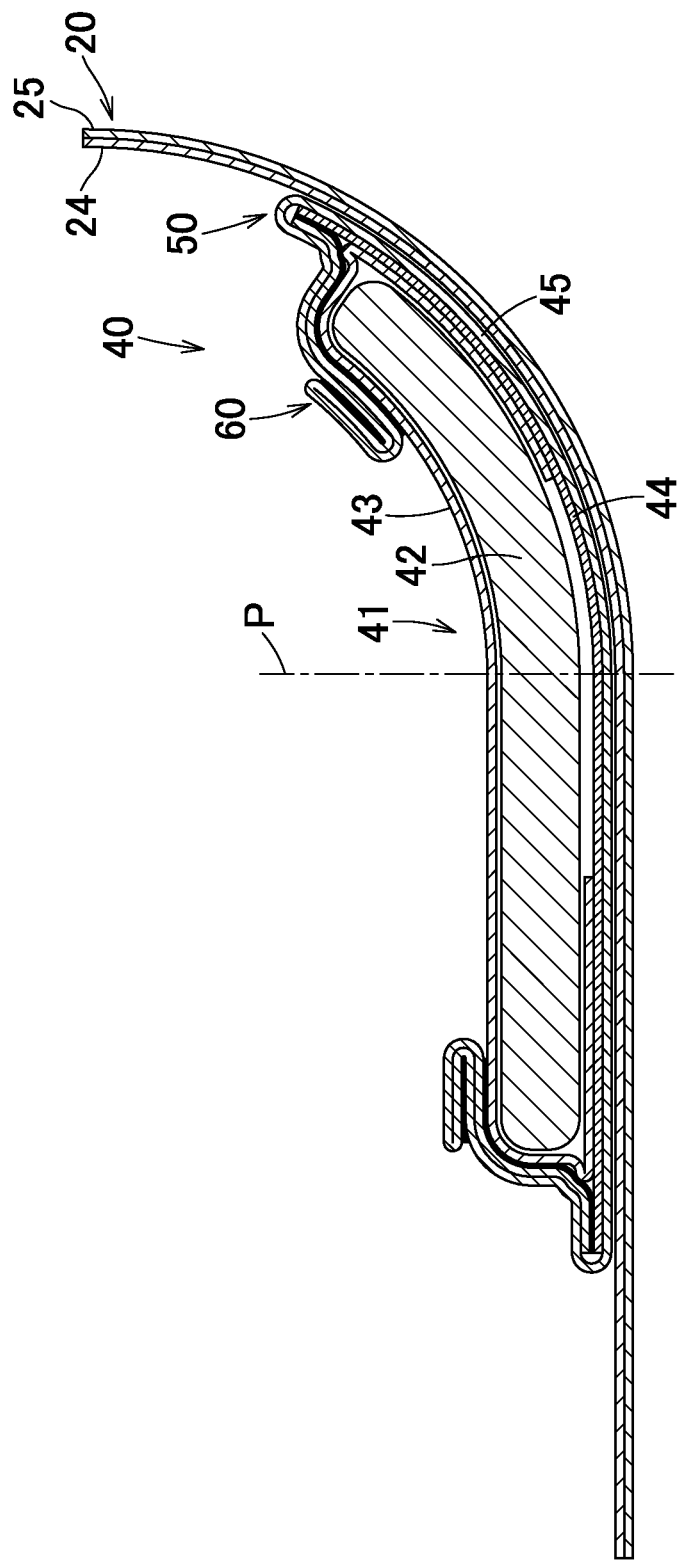
FIG. 4 is a sectional view taken along a line IV-IV in FIG. 2.
Figure 5:
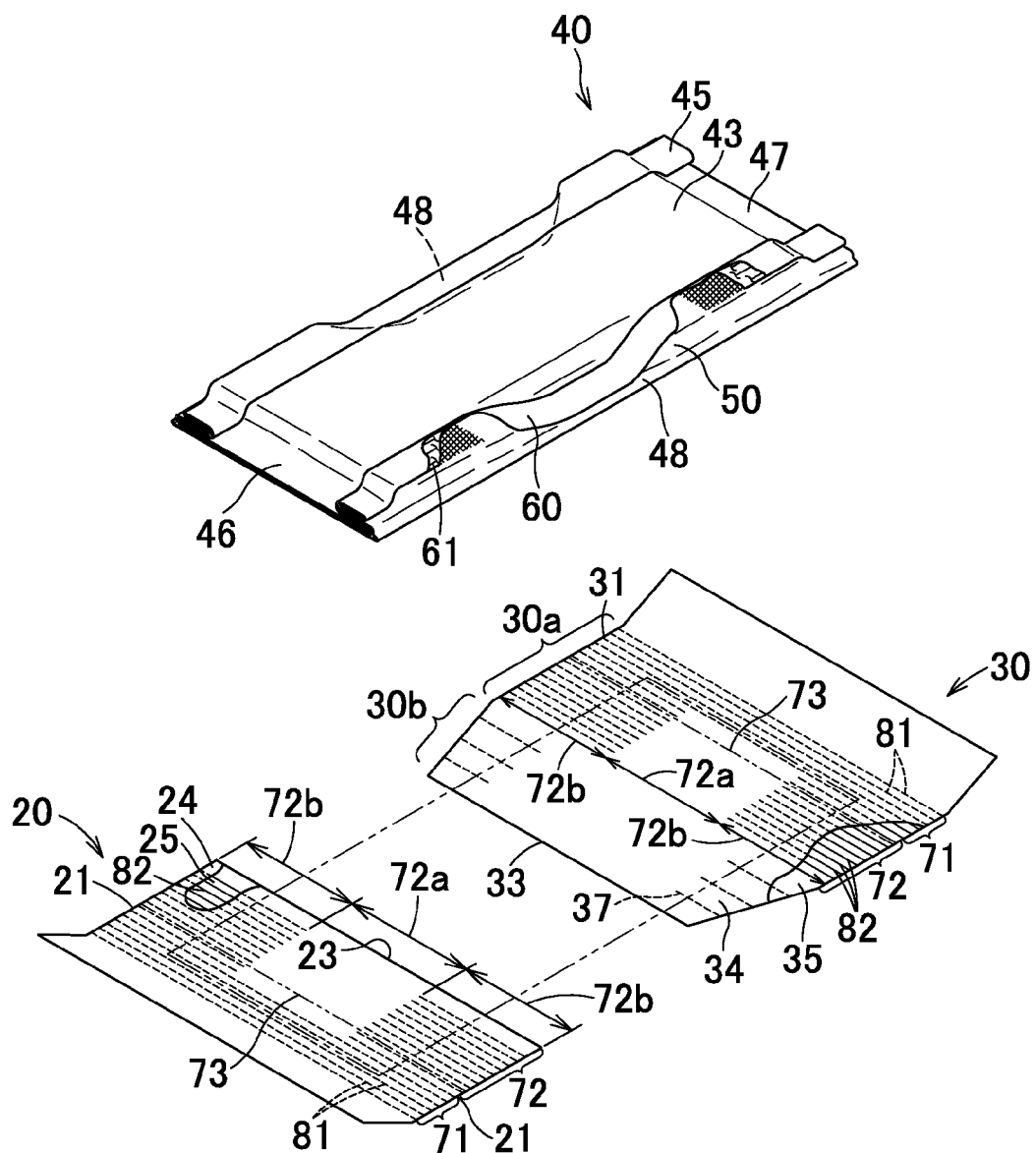
FIG. 5 is an exploded view corresponding to FIG. 2.

FIG. 1 is a perspective view showing a diaper 10 having a waist-opening and leg-openings both kept in annular states; FIG. 2 is a developed plan view of the diaper 10 as viewed its side facing the wearer's body. Respective elastic elements are stretched against contractile force thereof so as to maintain the diaper 10 in a flattened condition; FIG. 3 is a sectional view taken along the line in FIG. 2; FIG. 4 is a sectional view taken along a line IV-IV in FIG. 2; and FIG. 5 is an exploded view corresponding to FIG. 2. In the right half of FIGS. 3 and 4 about an imaginary longitudinal center line P-P, respective elastic members are shown to be in a contracted state.

The diaper 10 has a longitudinal direction Y, a transverse direction X, a side facing the wearer and a side facing the wearer's garment and includes a front waist region 11, a rear waist region 12 and a crotch region 13 extending between the front and rear waist regions 11, 12. The diaper 10 has the imaginary longitudinal center line P-P bisecting a dimension thereof in the transverse direction X and an imaginary transverse center line Q-Q bisecting a dimension thereof in the longitudinal direction Y. The diaper 10 has a substantially symmetric shape about the imaginary longitudinal center line P-P.

The diaper 10 includes front and rear waist members 20, 30 spaced from each other in the longitudinal direction Y and a crotch member 40 by the intermediary of which the front and rear waist members 20, 30 are connected. The front and rear waist members 20, 30 are bonded along respective opposite side edges 21, 21; 31, 31 to form seams. 14. These seams 14 define a waist-opening and a pair of leg-openings. The front and rear waist members 20, 30 respectively have outer ends 22, 32 cooperating with each other to form a peripheral edge of the waist opening and respectively have inner ends 23, 33 overlapping the crotch region 13 and thereby partially forming the leg-openings. The front and rear waist members 20, 30 respectively comprise topsheets 24, 34 lying on the side facing the wearer's body and backsheets 25, 35 lying on the side facing the wearer's garment.

Having bonded to the front waist member 20 along the respective opposite side edges 21, 31, the rear waist member 30 includes a waist fit region 30a overlapping the front waist member 20 so as to cover the wearer's waist and an extension region 30b extending from the waist fit region 30a toward the crotch region 13. A border between these waist fit region 30a and the extension region 30b is defined by an imaginary line 70. A dimension from the waist outer end 32 to the imaginary line 70 in the transverse dimension X is substantially equal to that from the front waist's outer end 22 of the front waist member 20 to the front waist's inner end 23 on the side of the crotch region 13.

A region extending from the front waist's outer end 22 of the front waist member 20 to the front waist's inner end 23 on the crotch region 13 is defined as the front waist region 11, a region extending from the rear waist' outer end 32 of the rear waist member 30 to the imaginary line 70, i.e., the waist fit region 30a is defined as the rear waist region 12, and a region extending from the imaginary line 70 to the front waist's inner end 23 is defined as the crotch region 13. The front and rear waist members 20, 30 cooperate with a part of the crotch member 40 to form a chassis according to the present invention.

The crotch member 40 includes a liquid-absorbent structure 41, a pair of gasket cuffs 50 and a pair of leakage barrier cuffs 60. The absorbent structure 41, in turn, includes a liquid-absorbent core 42, an inner sheet 43 lying on the side facing the wearer's body to cover the inner surface of the core 42, a leakage barrier sheet 44 adapted to cover the outer surface of the core 42 and an outer sheet 45 lying on the side facing the wearer's body to overlap the leakage barrier sheet 44. The core 42 may be formed, for example, from fluff pulp and/or super-absorbent polymer particles. Such core 42 has its dimension in the transverse direction X gradually reduced toward the imaginary transverse center line Q-Q to define a generally hourglass shape.

The core 42 has a dimension in the longitudinal direction Y is in a range of about 300 to 400 mm, preferably in a range of about 335 to 380 mm. The inner sheet 43 and the leakage barrier sheet 44 are respectively dimensioned to be larger than the dimension of the core 42 in the longitudinal direction Y, specifically, in a range of about 350 to 450 mm, preferably in a range of about 375 to 430 mm. Such liquid-absorbent structure 41 is formed outside of the core 42 as viewed in the longitudinal direction Y with front and rear end flaps 46, 47 each being formed of the inner sheet 43, the leakage barrier sheet 44 and the outer sheet 45. In these front and rear end flaps 46, 47, the inner sheet 43, the leakage barrier sheet 44 and the outer sheet 45 are bonded one to another with suitable adhesives such as well-known hot melt adhesives.

The core 42 is formed outside thereof as viewed in the transverse direction X with a pair of side flaps 48 (or gasket cuffs) including respective portions of the inner sheet 43, the leakage barrier sheet 44 of the outer sheet 45 extending outward beyond the periphery of the core 42. The sheets are bonded one to another with suitable adhesives such as well-known hot melt adhesives. Each of the side flaps 48 has its dimension in the transverse direction X in a range of about 170 to about 220 mm, preferably of about 190 mm.

As the inner sheet 43, for example, a liquid-pervious fibrous nonwoven fabric may be used. More specifically, for example, an air-through fibrous nonwoven fabric, a point-bonded fibrous nonwoven fabric or a span bonded fibrous nonwoven fabric each having a mass per unit area in a range of about 10 to about 25 g/m$^2$ may be used.

As the leakage barrier sheet 44, a moisture-pervious but liquid-impervious plastic film may be used in a manner that this sheet 44 may cover at least the entire bottom surface of the absorbent structure 41 and thereby may prevent body waste such as urine from leaking out of the diaper 10.

As the outer sheet 45, for example, a moisture-pervious but liquid-impervious fibrous nonwoven fabric may be used. More specifically, as this outer sheet 45, a spun bonded/melt blown/spun bonded (SMS) fibrous nonwoven fabric, a point-bonded fibrous nonwoven fabric or a spun bonded fibrous nonwoven fabric each having a mass per unit area in a range of about 10 to about 25 g/m$^2$ may be used.

The gasket cuffs 50 include the inner sheet 43 and the outer sheet 45 constituting the side flaps 48 and gasket elastic members 51 attached within respective sleeves formed of the outer sheet 45. Each of the gasket elastic members 51 includes two or more elastic yarns or threads extending in the longitudinal direction Y and attached thereto under tension and in a contractible manner.

The leakage barrier cuffs 60 are formed by folding portions of the outer sheet 45 extending outward beyond the gasket cuffs 50 substantially in a Z-shape above the absorbent structure 41. Between the layers defined by folding the outer sheet 45 in this manner, barrier elastic members 61 each including two or more elastic yarns or threads extend in the longitudinal direction Y and attached under tension and in a contractible manner. Each of these leakage barrier cuffs 60 is bonded at opposite ends thereof as viewed in the longitudinal direction to the associated gasket cuff 50 and not bonded thereto in the remaining region. In consequence, these leakage barrier cuffs 60 rise on the gasket cuffs 50 under contractile force of the barrier elastic members 61.

As illustrated in FIG. 3, the gasket cuffs 50 and the leakage barrier cuffs 60 rise so that the leakage barrier cuffs 60 may be spaced from the inner sheet 43 as the diaper 10 is put on the wearer's body. In this way, the leakage barrier cuffs 60 come in close contact with the areas in the vicinity of the wearer's inguinal regions. The gasket cuffs 50 also are elasticized in the longitudinal direction Y under the effect of the gasket elastic members 51 so that the gasket cuffs 50 are curved toward the diaper wearer's body and come in close contact around the wearer's thighs. Specifically, the leakage barrier cuffs 60 cooperate with the gasket cuffs 50 to form dual cuffs serving to prevent body waste such as urine from leaking out peripheries of the leg-openings.

The outer sheet 45 is bonded along front and rear ends 40a, 40b of the crotch member 40 and thereby the front and rear waist members 20, 30 are connected to the crotch member 40. The absorbent structure 41 on the crotch member 40 are attached so as to overlap the front and rear waist regions 11, 12. A dimension of the absorbent structure 41 in the longitudinal direction Y overlapping the front and rear waist regions 11, 12 is in a range of about 70 to about 90% of respective dimensions in the longitudinal direction Y of the front and rear waist regions 11, 12.

As illustrated in FIG. 2, the front and rear ends 40a, 40b of the crotch member 40 are covered with the inner and outer sheets 24, 25; 34, 35 folded back in the imaginary transverse center line Q-Q upon the upper surface of the crotch member 40. By covering the front and rear ends 40a, 40b with these sheets, it is possible to prevent the component material of the core 42 from falling off, on one hand, and it is possible to protect the wearer from experiencing any kind of skin trouble due to contact of the front and rear ends 40a, 40b with the wearer's skin.

The front and rear waist members 20, 30 extend from the waist outer ends 22, 32 toward the crotch region 13 and include first regions 71 overlapping the front and rear end flaps 46 of the absorbent structure 41, 47 and second regions 72 adjacent the respective first regions 71. The first and second regions 71, 72 which lie side-by-side are respectively bounded by associated imaginary lines 73. Both the first regions 71 and the second regions 72 circumferentially extend in the front and rear waist regions 11, 12 to form an annular shape.

According to the present embodiment, a distance in the longitudinal direction Y from the respective outer ends 22, 32 of the front and rear waist members to the front and rear end flaps 46, 47 of the absorbent structure 41, i.e., a dimension of the respective end flaps 46, 47 in the longitudinal direction Y is about 20 mm. A dimension in the longitudinal direction Y of the respective first regions 71 is about 23 mm and that dimension of the respective second regions 72 is about 67 mm. Sum of the dimensions of the first and second regions 71, 72 in the longitudinal direction Y respectively represents a dimension of the front and rear waist regions 11, 12, i.e., about 90 mm. Accordingly, the dimension of the respective first regions 71 in the longitudinal direction Y corresponds to about 26% of the front and rear waist regions 11, 12, respectively.

Between the respective top- and backsheets 24, 25; 34, 35 of the front and rear waist members 20, 30, first waist elastic members 81 and second waist elastic members 82 are attached to the first regions 71 and the second regions 72, respectively. Each of the first waist elastic members 81 includes two or more elastic yarns or threads continuously extending from the side edges 21, 31 to the opposite side edges 21, 31. According to the present embodiment, four (4) elastic yarns or threads each having fineness of about 470 dtex are attached so as to be spaced one from another in the longitudinal direction Y at an interval of about 5.5 mm. The first waist elasticizing members 81 may be attached to the first regions 71 under tension and in a contractible manner in the transverse direction X to elasticize the first regions 71 in the transverse direction X.

The second regions 72 are formed with inelastic zones 72a overlapping the core 42 and elastic zones 72b outside the inelastic zones 72a as viewed in the transverse direction X wherein the second waist elastic members 82 are attached to the elastic zones 72b so that the second waist elastic members 82 may respectively have inner ends 82a overlapping the core 42 and outer ends 82b lying on the side edges 21, 31. According to the present embodiment, eleven (11) elastic yarns or threads each having fineness in a range of about 470 to about 620 dtex are used as the second waist elastic members 82 and these elastic yarns or threads are spaced one from another in the longitudinal direction Y at an interval of about 5.5 mm. The second waist elastic members 82 may be attached to the respective elastic zones 72b under tension and in a contractible manner in the transverse direction X to elasticize the elastic zones 72b of the respective second regions 72 to elasticize these elastic zones 72b of the respective second regions 72 in the transverse direction X. The inelastic zones 72a have none of the second waist elastic members 82 attached thereto and, in consequence, these inelastic zones 72a are not elasticized.

The extension region 30b of the rear waist member 30 is provided with extension region elastic members 37 attached thereto in a manner that these elastic members 37 may have inner ends 37a overlapping the core 42 and outer ends 37b lying on the side edges 31. According to the present embodiment, each of the extension elastic members 37 includes two (2) elastic yarns or threads each having fineness of about 470 dtex and attached to the extension region 30b so as to be spaced from each other at an interval of about 25 mm the longitudinal direction Y. The extension region elastic members 37 may be attached to the extension region 30b under tension and in a contractible manner in the transverse direction X to elasticize the extension region 30b in the transverse direction X. In a similar fashion to the second regions 72, the extension region 30b also is locally free from the effect of the elastic members. Specifically, none of the elastic members is provided in a zone defined between the one inner end 37a and the opposite inner end 37a and not elasticized so long as this intermediate zone is concerned.

In the front and rear waist regions 11, 12 constructed as has been described above, tightening force of the first regions 71 is lower than tightening force of the second regions 72.

The tightening force was measured by a method as follows:

From the diaper 10 having the opposite side edges 21, 31 bonded together, the first and second regions 71, 72 were respectively cut out to prepare test pieces. For the regions partially occupied by the absorbent structure 41 were cut out together with the absorbent structure 41 so that such test pieces may include any portion of the absorbent structure 41. In each test piece contracted under the effect of the associated elastic member, a distance from the inner end of the seam line 14 to the inner end of the opposite seam line 14 was represented by SW and the corresponding distance in each test piece stretched in the transverse direction X against the contractile force of the associated elastic member was represented by PW. Dimension of each test piece in the longitudinal direction Y was represented by L.

The test piece was fixed to AUTOGRAPH (manufactured by Shimadzu Corporation in Japan) with an inter-chuck distance set to SW and stretched at a chuck velocity of 100 mm/min to a distance of 0.85×PW. From this point, the test piece was moved back in the inverted direction at the same velocity and a contractile force measured at a moment the inter-chuck distance reached 0.65×PW was determined as an entire tightening force Fa(N). From the entire tightening force Fa(N)/L×10, a tightening force per unit area F was calculated. The tightening force measured at the inter-chuck distance of 0.65×PW was specified as the entire tightening force Fa(N) on the basis of the empirical knowledge that 65% of PW is an average waist size of the diaper wearer.

Measurement result indicated that the tightening force F of the first region 71 was about 0.22 while the tightening force F of the second region 72 was about 0.30. More specifically, the tightening force F of the first region 71 was in a range of about 0.20 to 0.32 while the tightening fore F of the second region 72 was in a range of about 0.28 to 0.36. From such measurement result, the tightening force of the first region 71 is in a range of about 70 to 90%, preferably in a range of about 74 to 76% of the tightening force of the second region 72.

The tightening force of the first regions 71 set to be lower than that of the second regions 72 as has been described above facilitates the first regions 71 to be broadened when the front and rear waist members 20, 30 are broadened to put the diaper 10 on the wearer's body. Particularly, the waist-opening can be sufficiently broadened to facilitate the diaper 10 to be put on the wearer's body. Such diaper 10 can be smoothly put on the wearer lying face up, for example, the baby lying face up. If the wrinkles remain in the front and rear waist regions 11, 12 when the diaper 10 is put on the wearer lying face up, these wrinkles will friction the wearer's skin and uncomfortably irritate the skin. In the diaper 10 according to the present invention, such undesirable wrinkles can be substantially smoothed as the diaper 10 is put on the wearer's body.

The first regions 71 respectively have the dimension in the longitudinal direction Y reduced to about 26% of the front and rear waist regions 11, 12 so that the first regions 71 can be sufficiently broadened to smooth the wrinkles in these first regions 71 as the diaper 10 is broadened with the waist-opening held by the wearer's or care giver's hands. It should be appreciated that the dimension of the respective first regions 71 in the longitudinal direction Y is not limited to the above-mentioned value and, for example, by setting this dimension to 20 to 30% of the dimension of the front and rear waist regions 11, 12, the wrinkles can be easily smoothed and, in addition, the first regions 71 can be put in close contact with the wearer's body.

With the diaper 10 put on the wearer's body, even if the wrinkles on the top- and backsheets in the first regions 71 remain not completely smoothed and come in direct contact with the wearer's skin, these wrinkles come in soft contact with the wearer's skin since the tightening force of the first regions 71 is previously controlled to be relatively low. As a result, deep impressions of these wrinkles should not be left on the wearer's skin. In the respective first regions 71, at least one of the first waist elastic yarns or threads 81 overlaps the front or rear flap 46, 47 of the absorbent structure 41. With such arrangement, the front and rear end flaps 46, 47 can be put in close contact with the wearer's skin and thereby prevent body waste such as urine from leaking out beyond the front and rear ends 40a, 40b.

With regard to the second regions 72, the tightening force thereof may be set to be higher than that of the first regions 71 to assure the front and rear waist members 20, 30 to be put in close contact with the wearer's body. Despite such high tightening force, at least in zones of the second regions 72 overlapping the absorbent structure 41, the wrinkles formed by the top- and backsheets 24, 25; 34, 35 should not come in direct contact with the wearer's skin because the absorbent structure 41 is provided on these top- and backsheets 24, 25; 34, 35. In this way, it is possible to prevent impressions of the wrinkles from being left on the wearer's skin and to alleviate uncomfortable irritation of the skin due to the wrinkles. In addition, the second regions 72 include the inelastic zones 72a serving to restrict creation of the wrinkles in these inelastic zones 72a.

The present invention can be implemented in the optimal diaper 10 particularly for babies characterized in that the dimension of the diaper 10 in the longitudinal direction Y is relatively small. To assure that the absorbed amount of body waste such as urine is not significantly affected even when the diaper 10 is dimensioned to be relatively short in the longitudinal direction Y, it is desired to assure a sufficiently large size of the absorbent structure. In a consequence, an area ratio of the absorbent structure 41 to the diaper 10 will increase and about 70 to 90% of the dimension in the longitudinal direction Y of the front and rear waist regions 11, 12 will be occupied by the absorbent structure 41. Generally, stiffness of the absorbent structure 41 is a relatively high and it will be more and more difficult to broaden the diaper 10 in the transverse direction X and to put the diaper 10 on the wearer's body as the area ratio of the absorbent structure 41 to the diaper 10 increases. However, according to the present embodiment, the tightening force of the first regions 71 extending in the vicinity of the waist-opening controlled to be relatively low facilitates the diaper 10 to be broaden in the transverse direction X and thereby to put the diaper 10 on the wearer, particularly the baby lying face up.

While the dimension of the first region 71 in the longitudinal direction Y is set to about 23 mm according to the present embodiment, the dimension of the first region 71 is not limited to this value and it is also possible to set this dimension to a range of about 15 to about 35 mm. Likewise, it is also possible to set the dimension of the second region 72 to a range of about 55 to about 120 mm.

The dimension of the diaper 10 according to the present invention measured in the longitudinal direction Y is in a range of about 400 to about 520 mm, preferably in a range of about 410 to about 450 mm and 415 mm according to the present embodiment. Likewise, the dimension of the crotch member 40 as measured in the longitudinal direction Y is in a range of about 350 to about 450 mm, preferably in a range of about 370 to about 380 mm and about 375 mm according to the present embodiment. The dimension of the front waist member 20 defining the front waist region 11 as measured in the longitudinal direction Y is in a range of about 80 to about 130 mm, preferably in a range of about 85 to about 125 mm and about 90 mm according to the present embodiment. The dimension of the rear waist member 30 defining the rear waist region 12 as measured in the longitudinal direction Y is in a range of about 150 to about 190 mm, preferably in a range of about 155 to about 185 mm and about 155 mm according to the present embodiment.

While two or more elastic yarns or threads are used to elasticize the front and rear waist members 20, 30 in the transverse direction X according to the present embodiment, the means used to elasticize these waist members 20, 30 is not limited to these elastic yarns or threads and it is also possible to use various types of elastic members such as elastic sheets or ribbon-like elastic members. Likewise, various types of elastic members may be used as the gasket elastic member 51 and the barrier elastic member 61. While the core 42 having the dimension in the transverse direction X smaller in the middle section than in the front and rear sections is used according to the present embodiment, it is also possible to use the core 42 having the uniform dimension in the transverse direction X.

Second Embodiment

Figure 6:
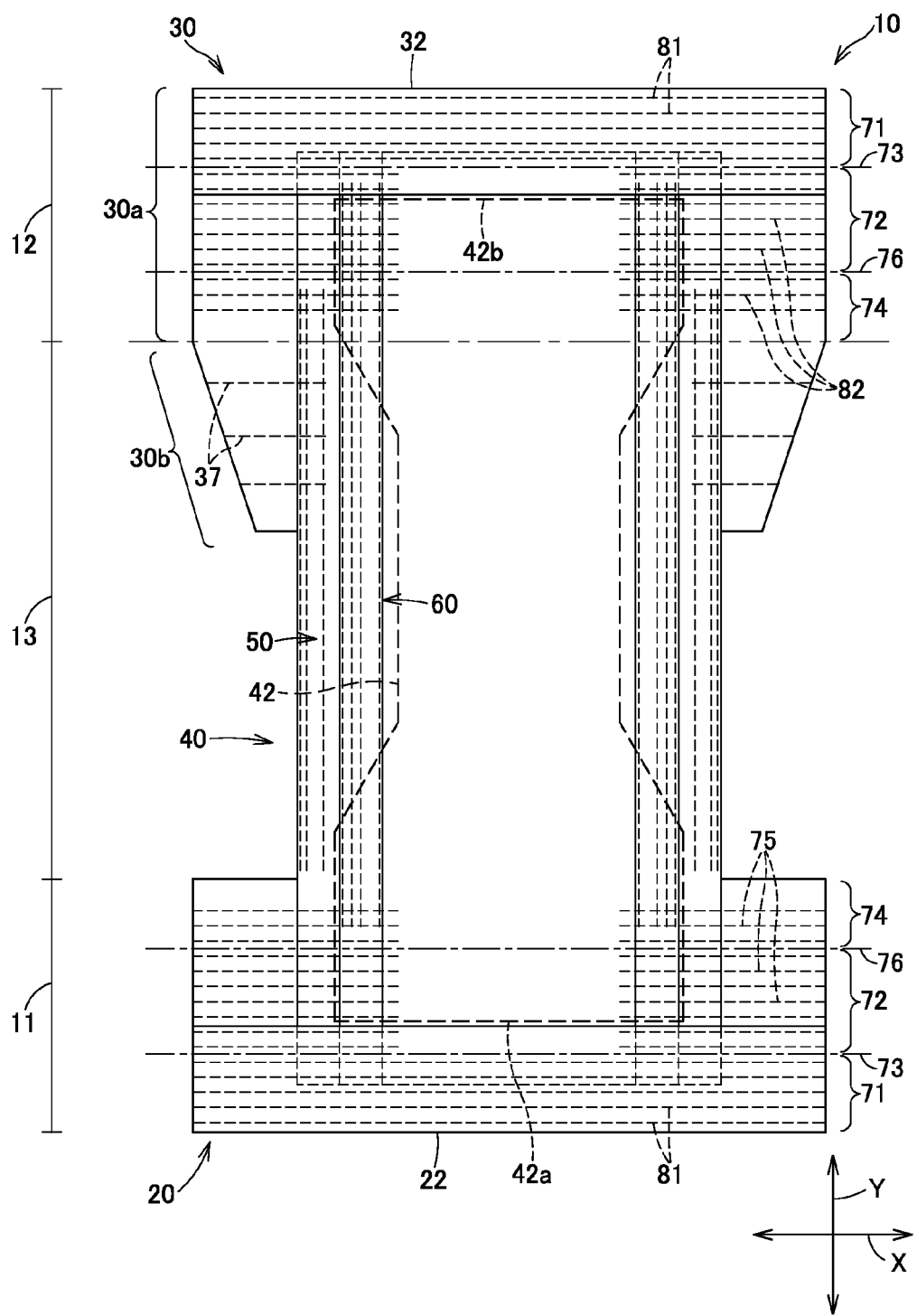
FIG. 6 is a developed plan view of the diaper according a second embodiment of the present invention as viewed from the side facing the wearer's body.

FIG. 6 illustrates a second embodiment of the present invention characterized in that there are provided third regions 74 extending adjacent the respective second regions 72 on the side of the crotch region. The features other than this feature are similar to those in the first embodiment. The similar features are designated by the reference numerals similar to those used in the first embodiment and will not be repetitively describe in details.

The front and rear waist regions 11, 12 respectively comprise the first regions 71, the second regions 72 and the third regions 74. The second regions 72 and the third regions 73 are respectively bounded by imaginary lines 76. According to the present embodiment, the second regions 72 respectively have a dimension in the longitudinal direction Y of about 44 mm and the third regions 74 respectively have a dimension in the longitudinal direction Y of about 27.5 mm. However, the present invention is not limited by these values. Specifically, the dimension of the second regions 72 may be appropriately selected in a range of about 27 to about 50 mm and that of the third regions 74 may be appropriately selected in a range of about 25 to about 36 mm. It should be understood here that the dimension of the respective first regions 71 in the longitudinal direction Y is the same as that in the first embodiment.

The values of tightening force provided by the first and second regions 71, 72 are the same as those having been described with respect to the first embodiment. The tightening force of the respective third regions 74 may be selected in a range of about 0.16 to about 0.28 and is set to about 0.18 according to the present embodiment. The method for measurement of the tightening force is the same as that employed for the first embodiment. The tightening force of the respective second regions 72 may be higher than that of the respective third regions 74 by about 20 to about 50% and, according to the present embodiment, this tightening force is set to be higher than that of the respective third regions 74 by about 40%.

The third regions 74 formed adjacent the respective second regions 71 on the side of the crotch region 13 contribute to improvement in feeling to wear the diaper 10. The third regions 74 are adapted to come in contact with the wearer's inguinal region and, if the tightening force of these third regions 74 is extremely high, particularly the top- and backsheets 24, 25 of the front waist member 20 should dig into the wearer' inguinal region. However, by controlling the tightening force of these third regions 74 to be relatively low, the digging into the inguinal region can be restricted. On the other hand, the second regions 72 having relatively high tightening force assure these regions 72 to be put in close contact with the wearer's body. In this way, the fitness as well as the leakage barrier function should not be deteriorated. The tightening force of the respective second regions 72 may be set to be higher than that of the third regions 74 by about 20 to about 50% to assure that the second regions 72 are kept in close contact with the wearer's body and at the same time the third regions 74 are prevented from digging into the wearer's inguinal region.

While the tightening force of the first region and the tightening force of the second region in the front waist member 20 are set to be the same as those in the rear waist member 30 according to both the first embodiment and the second embodiment, it is possible to differentiate the tightening force of the first region and the tightening force of the second region in the front waist member 20 from those in the rear waist member 30. For example, the tightening force of the first region in the rear waist member 30 may be set to be lower than that in the front waist member 20 to make it further easier to broaden the rear waist region 12 in the transverse direction X. It makes easier to put the diaper particularly on the wearer lying face up. While the distances from the respective waist ends 22, 32 to the front and rear ends 42a, 42b of the core 42 are the same according to the first and second embodiments, these distances also may be differentiated.

REFERENCE SIGNS LIST

10 diaper (wearing article)
11 front waist region
12 rear waist region
13 crotch region
41 liquid-absorbent structure
42 core
42a front end
42b rear end
43 inner sheet (cover sheet)
45 outer sheet (cover sheet)
46 front flap
47 rear flap
71 first region
72 second region
72a inelastic zone
72b elasticized zone
74 third region
81 first waist elasticizing member
82 second waist elasticizing member
X transverse direction
Y longitudinal direction

The invention claimed is:

1. A wearing article having a longitudinal direction and a transverse direction, the wearing article comprising:
    a chassis comprising a side facing the wearer's body, a side facing the article wearer's garment, a front waist region, a rear waist region and a crotch region extending between the front and rear waist regions;
    a liquid-absorbent structure extending across the crotch region into the front and rear waist region; and
    waist elastic members attached to the front and rear waist regions under tension and in a contractible manner in the transverse direction wherein the liquid-absorbent structure includes a liquid-absorbent core, a cover sheet used to cover the core and front and rear end flaps lying outside front and rear ends of the core as viewed in the longitudinal direction and formed of the cover sheet, wherein:

the liquid-absorbent structure overlapping the front and rear waist regions has a dimension in the longitudinal direction corresponding to 70 to 90% of a dimension in the longitudinal direction of the respective front and rear waist regions and the front and rear waist regions extend from a waist-opening end to the crotch region and at least include first regions at least partially overlapping the front and rear end flaps and second regions extending adjacent the first regions; and the first regions are elasticized over the entire area thereof by first waist elastic members in the transverse direction, the second regions respectively include inelastic zones overlapping the core and elastic zones lying outside the inelastic zones outside as viewed in the transverse direction and elasticized by second waist elastic members wherein tightening force of the first regions are set to be lower than that of the second regions such that the tightening force of the first regions corresponds to 70 to 90% of the tightening force of the second regions and the tightening force of the first region in the rear waist member is lower than the tightening force of the first region in the front waist member.

2. The wearing article defined by claim 1, wherein the front and rear waist regions respectively include third regions extending adjacent the second regions on the side of the crotch region, the front and rear waist regions respectively divided into the first regions, the second regions and the third regions and the tightening force of the third regions is set to be lower than that of the second regions.

3. The wearing article defined by claim 2, wherein the tightening force of the second regions is set to be higher than that of the third regions by 20 to 50%.

* * * * *